United States Patent
Goedeke

(10) Patent No.: US 7,149,581 B2
(45) Date of Patent: Dec. 12, 2006

(54) PATIENT MONITORING DEVICE WITH MULTI-ANTENNA RECEIVER

(75) Inventor: Steven D. Goedeke, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 600 days.

(21) Appl. No.: 10/355,855

(22) Filed: Jan. 31, 2003

(65) Prior Publication Data

US 2004/0152953 A1 Aug. 5, 2004

(51) Int. Cl.
*A61N 1/08* (2006.01)
(52) U.S. Cl. .............. 607/32; 607/30; 607/31; 607/59; 607/60
(58) Field of Classification Search ............ 607/30–32, 607/50–60; 600/522; 128/903–904
See application file for complete search history.

(56) References Cited

U.S. PATENT DOCUMENTS

| | | | |
|---|---|---|---|
| 5,626,630 A * | 5/1997 | Markowitz et al. | 607/60 |
| 5,904,708 A | 5/1999 | Goedeke | 607/18 |
| 6,169,925 B1 | 1/2001 | Villaseca et al. | 607/60 |
| 6,418,346 B1 * | 7/2002 | Nelson et al. | 607/59 |
| 6,490,487 B1 | 12/2002 | Kraus et al. | 607/60 |
| 2001/0047314 A1 | 11/2001 | Linberg | 705/28 |
| 2002/0072785 A1 * | 6/2002 | Nelson et al. | 607/60 |
| 2002/0103508 A1 * | 8/2002 | Mathur | 607/5 |
| 2003/0099315 A1 * | 5/2003 | Beaudin | 375/347 |
| 2004/0088027 A1 * | 5/2004 | Burnes et al. | 607/60 |
| 2004/0117204 A1 * | 6/2004 | Mazar et al. | 705/2 |

FOREIGN PATENT DOCUMENTS

| | | |
|---|---|---|
| EP | 0 602 459 B1 | 11/1999 |
| WO | WO 00/47109 | 8/2000 |
| WO | WO00/51488 * | 9/2000 |

* cited by examiner

*Primary Examiner*—Robert E. Pezzuto
*Assistant Examiner*—Jessica L. Reidel
(74) *Attorney, Agent, or Firm*—Michael C. Soldner; Girma Wolde-Michael

(57) ABSTRACT

A patient monitoring device incorporates a receiver capable of single-antenna or multi-antenna operation. Multi-antenna operation permits the monitoring device to take advantage of spatial diversity for improved communication with an implantable medical device in the presence of fading. However, the small size of many patient monitoring devices can make the incorporation of multiple antennas difficult. To permit spatial diversity operation, a base station includes at least a second antenna that can be coupled to the patient monitoring device. Alternatively, the base station may have one or more high quality antennas that are used by patient monitoring device instead of the antenna in the patient monitoring device when the patient monitoring device is coupled to the base station.

25 Claims, 7 Drawing Sheets

PATIENT MONITORING DEVICE WITH MULTI-ANTENNA RECEIVER

TECHNICAL FIELD

This invention relates to implantable medical devices and, more particularly, patient monitoring devices for communication with implantable medical devices.

BACKGROUND

Implantable medical devices typically include a wireless telemetry link that permits communication between the implanted medical device and an external programmer or patient monitoring device. The wireless telemetry link may permit the transmission of commands from a programmer or patient monitoring device to the implantable medical device, e.g., to program new features or functionality into the implantable medical device. Also, the wireless telemetry link may permit the programmer or monitoring device to interrogate the implantable medical device to obtain stored operational information and sensed physiological parameters.

A transceiver and antenna typically are located within a housing associated with the implantable medical device. Conventional programmers and patient monitoring devices incorporate a transceiver head that is placed in close proximity to the implantable medical device for programming and interrogation. The transceiver head may be coupled to the programmer or monitoring device via a cord. More recently, telemetry systems for implantable medical devices have eliminated the need for a transceiver head in the programmer or monitoring device. Instead, various wireless communication techniques have been implemented to permit increased transmission distances between the implantable medical device and the programmer or patient monitoring device.

Improved wireless communication techniques may permit the implantable medical device to be located several meters from the programmer or monitoring device, providing the patient with increased mobility during programming and interrogation. In some cases, a patient monitoring device may be placed within the home of a patient, and configured to monitor the implantable medical device by wireless telemetry during the course of the patient's daily routine. In addition, some patient monitors may take the form of portable devices that can be carried with the patient, e.g., much like a personal digital assistant (PDA) or cell phone.

SUMMARY

In general, the invention is directed to a patient monitoring device having a receiver capable of both single-antenna and multi-antenna operation. Multi-antenna operation permits the monitoring device to take advantage of spatial diversity for improved communication with an implantable medical device in the presence of fading. However, the small size of many patient monitoring devices can make the incorporation of multiple antennas difficult. To permit spatial diversity operation, the invention provides a base station having a second antenna that can be coupled to the patient monitoring device. Alternatively, the base station may have one or more high quality antennas that are used by patient monitoring device instead of the antenna in the patient monitoring device when the patient monitoring device is coupled to the base station.

The patient monitoring device may provide multi-antenna operation when it is coupled to the base station, and single-antenna operation when it is not coupled to the base station. Alternatively, the patient monitoring device may use a high quality antenna provided in the base station when it is coupled to the base station. The base station may take the form of a docking station, platform, cradle or the like that receives the patient monitoring device and couples an antenna to the patient monitoring device, e.g., for spatial diversity or increased antenna quality. The patient monitoring device may provide an adaptable receiver and transmitter capable of operating in either the single-antenna or multi-antenna mode. In this manner, the invention can achieve spatial diversity without consuming additional space within the monitoring device for a second antenna.

In one embodiment, the invention provides a system comprising an implantable medical device, a base station having a first antenna, and a monitoring device having a second antenna, wherein the monitoring device receives wireless signals from the implantable medical device via both the first antenna and the second antenna when the monitoring device is coupled to the base station.

In another embodiment, the invention provides a monitoring device for monitoring an implanted medical device, the device comprising a first antenna, a wireless receiver coupled to the first antenna to process signals received from the implanted medical device via the first antenna, and a terminal to couple the receiver to a second antenna associated with a base station to process signals received from the implanted medical device via the second antenna.

In a further embodiment, the invention provides a method comprising receiving wireless signals from an implantable medical device via both a first antenna associated with a monitoring device and a second antenna associated with a base station when the monitoring device is coupled to the base station, and receiving the wireless signals via only the first antenna when the monitoring device is not coupled to the base station.

In yet another embodiment, the invention provides a monitoring device for monitoring an implanted medical device, the monitoring device comprising a wireless receiver to receive signals transmitted by a transmitter, wherein the receiver receives the signals via a first antenna and a second antenna when the monitoring device is coupled to a second device and receives signals via only the first antenna when the monitoring device is not coupled to the second device.

In another embodiment, the invention provides a base station comprising an antenna, and a terminal to connect the antenna to a monitoring device for monitoring an implantable medical device when the monitoring device is coupled to the base station.

The invention includes various aspects. For example, the invention may permit spatial diversity operation in a patient monitoring device without the need to incorporate an additional antenna in the device. Instead, the patient monitoring device may provide single-antenna operation when it is not coupled to the base station and multi-antenna operation when it is coupled to the base station. Alternatively, the patient monitoring device may use a high quality antenna provided in the base station instead of the device antenna.

When the patient monitoring device is not coupled to the base station, the patient is more likely to carry the monitoring device in closer proximity to the implantable medical device. In this case, single-antenna operation may be sufficient. When the patient monitoring device is not carried by the patient and, hence, may be further away from the implantable medical device, placing the patient monitoring device in the base station provides improved communication via spatial diversity techniques or via a higher quality antenna. In this manner, the invention may improve overall reliability of communication between the patient monitoring device and the implantable medical device.

The details of one or more embodiments of the invention are set forth in the accompanying drawings and the description below. Other aspects of the invention will be apparent from the description and drawings, and from the claims.

DETAILED DESCRIPTION

Figure 1:
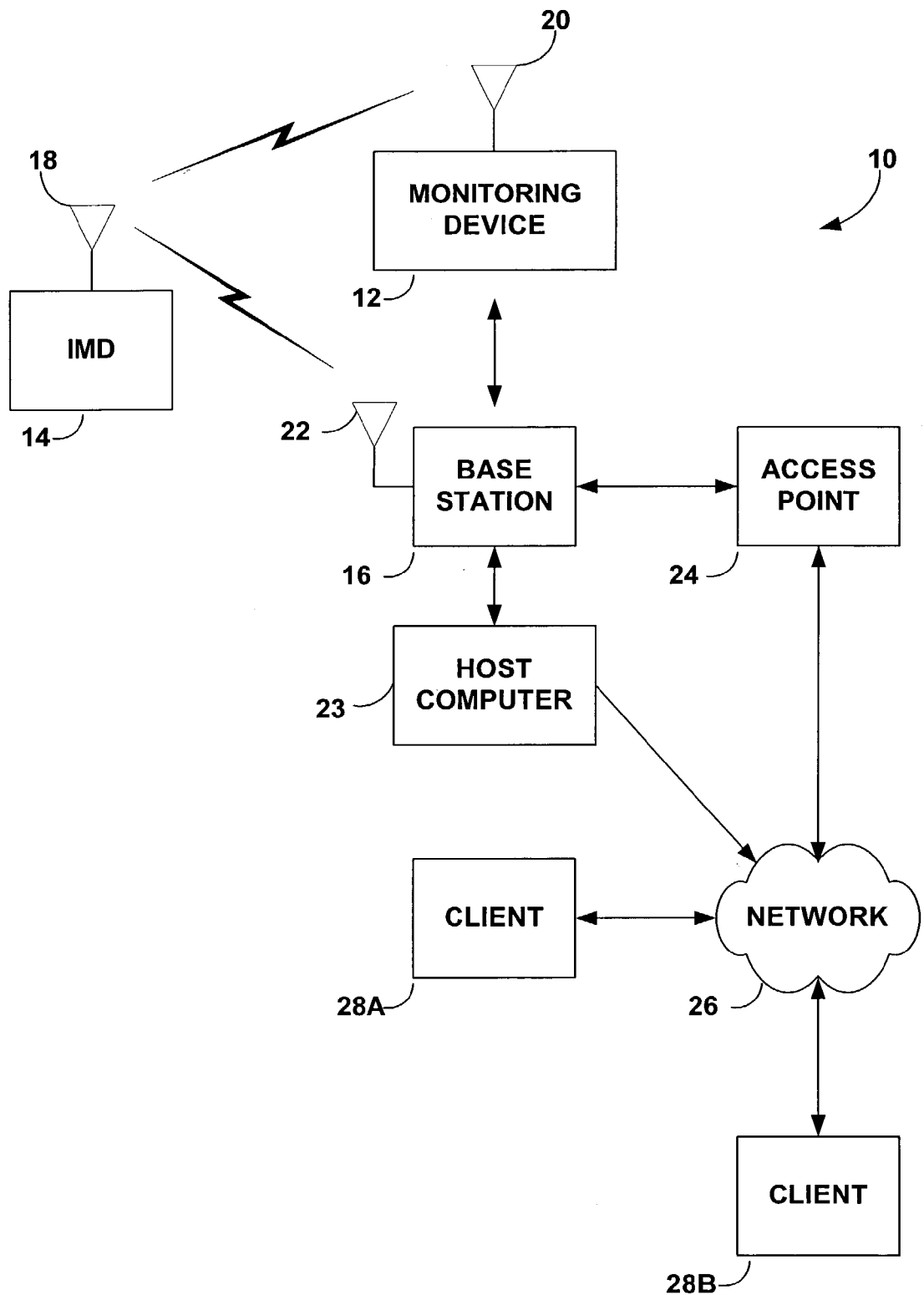
FIG. 1 is a block diagram illustrating a system including a patient monitoring device capable of multi-antenna operation in accordance with the invention.

FIG. 1 is a block diagram illustrating a system 10 including a patient monitoring device 12 capable of multi-antenna operation in accordance with an embodiment of the invention. As shown in FIG. 1, system 10 may include monitoring device 12, an implantable medical device ("IMD") 14, and a base station 16. IMD 14 transmits signals via antenna 18 to patient monitoring device 12. Monitoring device 12 includes an antenna 20. Base station 16 includes an antenna 22. Monitoring device 12 may be used independently of base station 16 or coupled to the base station.

In accordance with the invention, monitoring device 12 is configured for single-antenna operation or multi-antenna operation. In particular, monitoring device 12 uses antenna 20 for communication with IMD 14 when the monitoring device is not coupled to base station 16. When monitoring device 12 is coupled to base station 16, however, the monitoring device uses not only antenna 20, but also antenna 22 provided in base station 16. In this manner, monitoring device 12 can take advantage of spatial diversity to communicate with IMD 14 when the monitoring device is coupled to base station 16.

As further shown in FIG. 1, base station 16 may be coupled to a host computer 23 that provides access to a network 26. Alternatively, base station 16 may be coupled directly to an access point 24 that provides to network 26. Network 26 may be a local area network, wide area network or global computer network, such as the World Wide Web, and provides communication between monitoring device 12 and one or more network clients 28. Monitoring device 12 or an application running on host computer 23 may gather and forward data obtained from IMD 14 to the clients 28. Clients 28 may be associated with monitoring physicians and may run automated applications to process information received from monitoring device 12 via network 26.

Base station 16 may serve multiple purposes. In addition to providing a second antenna for spatial diversity, base station 16 may operate as a docking station to permit wired or wireless communication of monitoring device 12 with host computer 23 or network access point 24. In some embodiments, base station 16 may facilitate synchronization of data stored within monitoring device 12 with data stored by host computer 23 or one or more of clients 28. In this sense, base station 16 may operate much like a "synch" cradle used with many conventional PDAs. Also, base station 16 may serve to charge a rechargeable battery within monitoring device 12 when the monitoring device is coupled to, e.g., docked within, the base station.

Monitoring device 12 may be used with a variety of different IMDs 14 including a cardiac stimulator, a neuro stimulator, a drug delivery device, and a physiological sensor device. One example of an implantable medical device 14 is a pacemaker. Another example of an implantable medical device is a pacemaker-cardioverter-defibrillator ("PCD"). Other examples include an implantable brain stimulator, an implantable gastric system stimulator, an implantable nerve stimulator or muscle stimulator, an implantable lower colon, an implantable drug or beneficial agent dispenser or pump, an implantable cardiac signal loop or other type of recorder or monitor, an implantable gene therapy delivery device, an implantable incontinence prevention or monitoring device, an implantable insulin pump or monitoring device, and so on. IMD 14 may continuously collect operational information and physiological information. The physiological information may include heart rate, heart rate variability, blood glucose levels, oxygen saturation, partial pressure of oxygen in the blood, blood pressure, baro-reflex measures, electrogram morphologies, lung wetness, and the like.

Antenna 20 of monitoring device 12 is coupled to a wireless receiver to process signals received from IMD 14. In addition, antenna 20 may be coupled to a wireless transmitter. Accordingly, monitoring device 12 may be designed for one-way or two-way communication with IMD 14. A transmitter may be used by monitoring device 12 to program IMD 14. Also, in accordance with the invention, monitoring device 12 may provide either single-antenna or multiple-antenna operation. In this manner, monitoring device 12 may be configured to provide a spatial diversity mode in which the receiver processes signals received via both antenna 20 and antenna 22.

Monitoring device 12 may take a variety of forms. For example, monitoring device 12 may be a dedicated monitoring device. Alternatively, monitoring device 12 may be integrated with other device functionality. In particular, monitoring device 12 may be integrated with a cell phone, a PDA, or the like. The monitoring device 12 may receive wireless signals from IMD 14 via only antenna 20 when it is not coupled to base station 16. Additionally, the monitoring device 12 may receive signals from IMD 14 via both antenna 20 and antenna 22 when it is coupled to base station 16.

Figure 2:
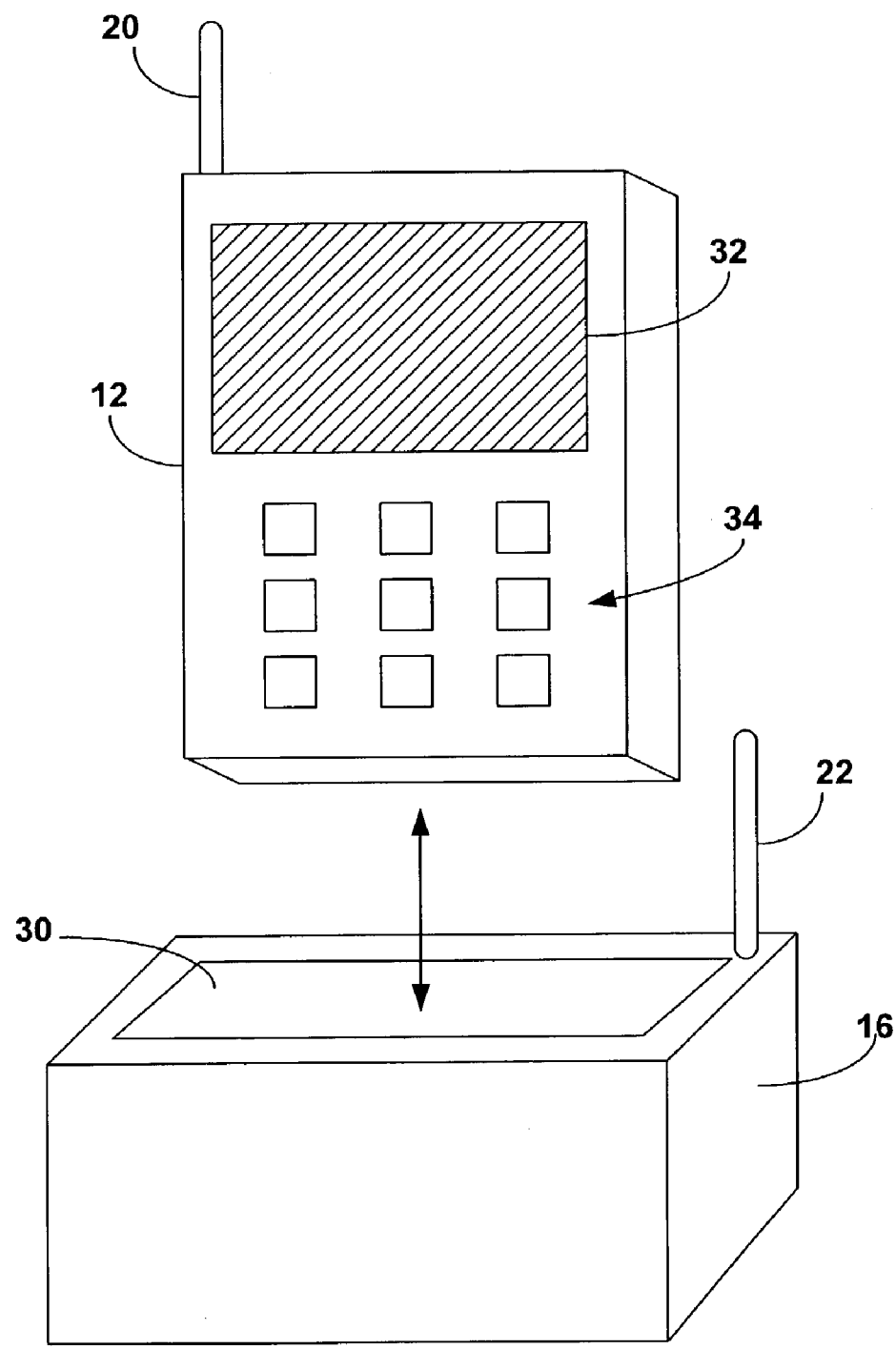
FIG. 2 is a block diagram illustrating a patient monitoring device and a base station in accordance with the invention.

FIG. 2 is a block diagram illustrating a patient monitoring device 12 and a base station 16 in accordance with one embodiment of the invention. As shown in FIG. 2, base station 16 may define a cradle, platform or other support to receive monitoring device 12 and provide engagement between contact terminals associated with the base station and the monitoring device. In particular, monitoring device 12 may include a contact terminal to couple the receiver to a second antenna 22 provided in base station 16. Base station 16 may include a reciprocal terminal that engages the contact terminal in monitoring device 12 to couple antenna 22 to the monitoring device. Alternatively, in other embodiments, antenna 22 of base station 16 may be coupled to monitoring device 12 via a cable.

In the example of FIG. 2, monitoring device 12 includes antenna 20, a display screen 32 and user input media such as an array of buttons 34. Base station 16 includes antenna 22, and a cradle-like receptacle to receive monitoring device 12 and facilitate engagement of reciprocal contact terminals in the monitoring device and the base station. Base station 16 may be coupled to a source of power via a power cord (not shown in FIG. 2). In addition, base station 16 may include communication links to host computer 23 or access point 24. FIG. 2 depicts antenna 22 is shown as protruding from base station 16. In other embodiments, however, antenna 22 could be a dedicated, free-standing antenna that is coupled to base station 16 via a cable. Alternatively, antenna 22 could be integrated with a power cord associated with base station 16, or embedded within the housing of the base station.

In some embodiments, base station 16 may further include radio circuitry to process wireless signals received via antenna 22. In other words, base station 12 may provide some of the circuitry necessary to process one of the spatial diversity channels involved in transmitting or receiving signals via multiple antennas 20, 22. In this manner, base station 16 may further reduce the size, power consumption and complexity of monitoring device 12. Alternatively, such circuitry may be provided in monitoring device 12, with base station 16 providing a simple electrical pass-through from antenna 22 and the monitoring device.

In accordance with the invention, a monitoring device 12 that is capable of single-antenna or multi-antenna communication can provide more reliable communication between IMD 14 and the monitoring device. Monitoring device 12 can take advantage of spatial diversity without the need to incorporate an additional antenna in the monitoring device. Instead, monitoring device 12 cooperates with its own base station 16 to provide spatial diversity, thereby reducing the size, cost and complexity of the monitoring device. The space required for the second antenna 22, and perhaps radio circuitry for processing signals received and transmitted by the second antenna, can be provided by base station 16.

Figure 3:
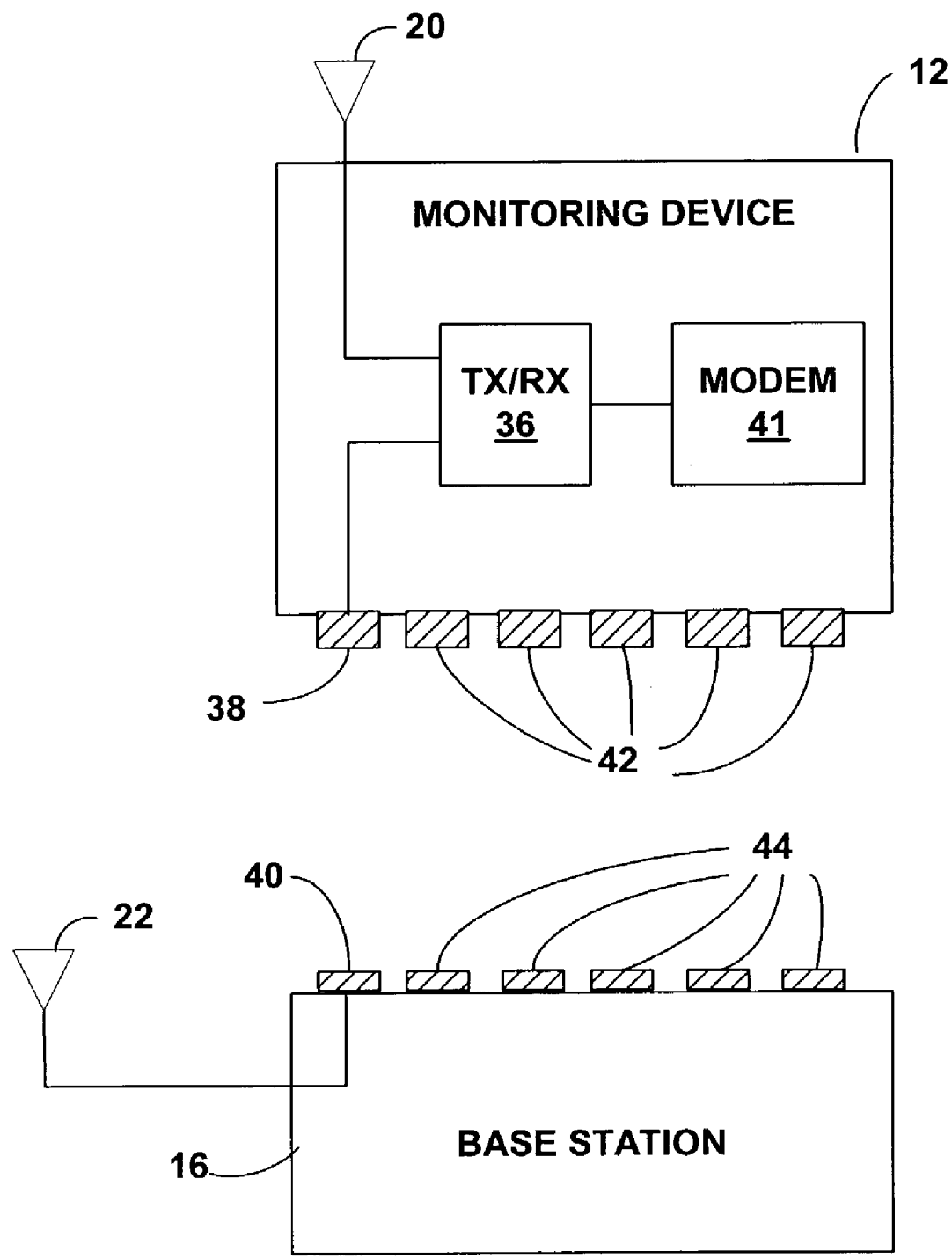
FIG. 3 is a block diagram illustrating connection of a patient monitoring device and a base station in accordance with an embodiment of the invention.

FIG. 3 is a block diagram illustrating connection of patient monitoring device 12 and base station 16 in accordance with an embodiment of the invention. As shown in FIG. 3, monitoring device 12 includes transmitter/receiver (TX/RX) circuitry 36 to process signals received and transmitted by antenna 20 in monitoring device 12 and antenna 22 in base station 16. In particular, TX/RX 36 may be coupled to antenna 20 and a terminal 38. In addition, TX/RX 36 may be coupled to a modem 41 that modulates and demodulates signals transmitted and received via antenna 20 or both antennas 20, 22.

When monitoring device 12 rests in or on base station 16, terminal 38 contacts a terminal 40 in base station 16. Terminal 40 may be coupled to antenna 22 or, alternatively, radio circuitry with base station 16 that processes signals transmitted and received by antenna 22. Additional terminals 42, 44 may be provided on monitoring device 12 and base station 16, respectively, for exchange of data and battery charging current.

Monitoring device 12 processes signals exchanged with IMD 14. TX/RX 46 in monitoring device 12 may include a spatial diversity receiver and transmitter to process signals received and transmitted via antenna 20, 22. In other embodiments, monitoring device 12 may not include a transmitter and instead serves only to gather data from IMD 14. When monitoring device 12 is not coupled to base station 12, it receives signals via antenna 20. When monitoring device 12 is coupled to base station 12, however, it receives signals via both antennas 20, 22. Accordingly, TX/RX 44 may provide an auto-detection feature that automatically detects the connection of antenna 22 via contact terminals 38, 40.

Figure 4:
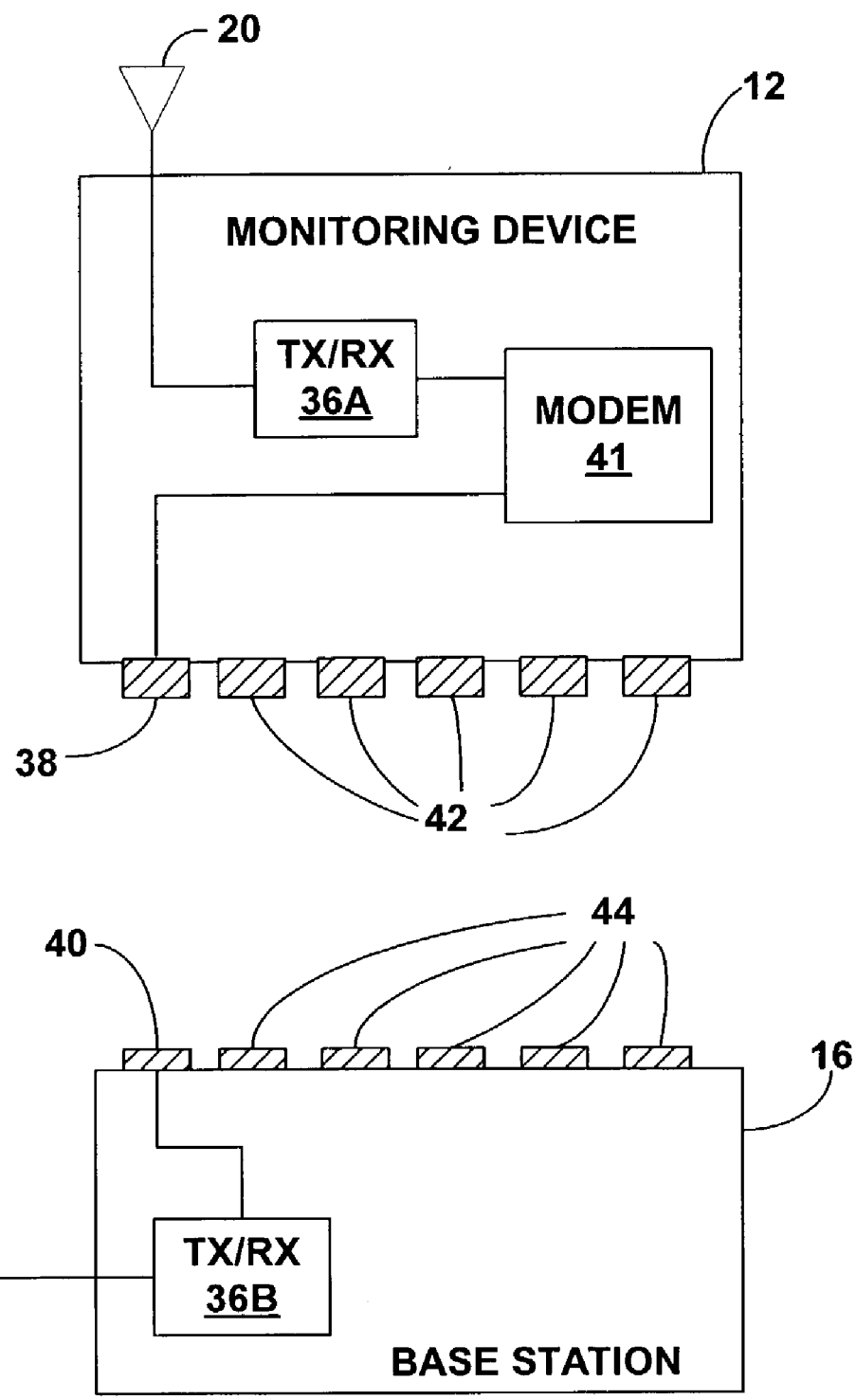
FIG. 4 is a block diagram illustrating connection of a patient monitoring device and a base station in accordance with another embodiment of the invention.

FIG. 4 is a block diagram illustrating connection of patient monitoring device 12 and base station 16 in accordance with another embodiment of the invention. FIG. 4 conforms substantially to FIG. 3 but illustrates incorporation of TX/RX circuitry within base station 16 to process signals for antenna 22. In particular, first TX/RX circuitry 36A is provided in monitoring device 12 to process signals for antenna 20, and second TX/RX circuitry 36B is provided in base station 16 to process signals for antenna 22. TX/RX circuitry 36A, 36B may perform filtering, amplification, upconversion or downconversion of signals transmitted or received by antennas 20, 22, respectively. Accordingly, each of TX/RX circuitry 36A, 36B may be coupled to modem 41. However, TX/RX circuitry 36B is coupled to modem 41 via terminals 38, 40 upon coupling of monitoring device 12 with base station 16.

Figure 5:
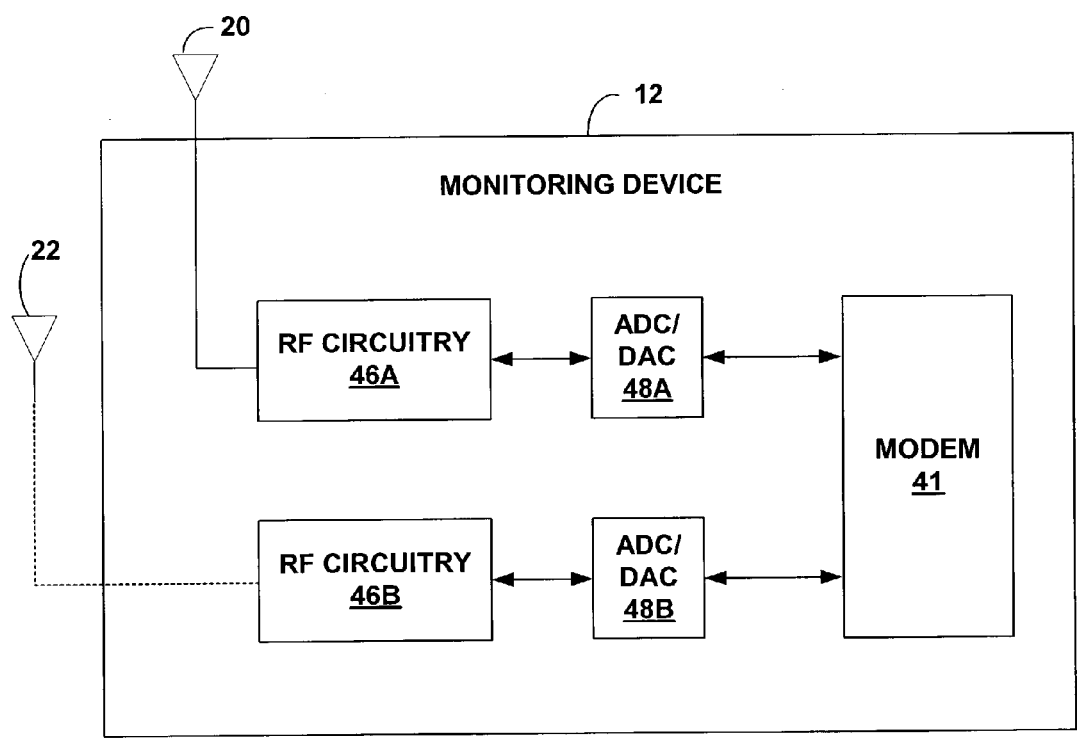
FIG. 5 is a block diagram illustrating spatial diversity circuitry associated with a patient monitoring device.

FIG. 5 is a block diagram illustrating spatial diversity circuitry associated with a patient monitoring device 12. As shown in FIG. 5, monitoring device may include separate channels for processing signals transmitted or received by antennas 20, 22 to spatial diversity. One channel includes radio frequency (RF) circuitry 46A and analog-to-digital (ADC)/digital-to-analog (DAC) circuitry 48A to process signals for antenna 20. A second channel includes RF circuitry 46B and ADC/DAC circuitry 48B to process signals for antenna 22. RF circuitry 46A, 46B may include conventional filtering, amplification, downconversion, and upconversion circuitry to process signals transmitted and received by antennas 20, 22, respectively. Also, ADC/DAC circuitry 48A, 48B converts digital signals generated by modem 41 into analog signals for transmission on antennas 20, 22, and converts analog signals received by antennas 20, 22 to digital signals for demodulation by modem 41.

Figure 6:
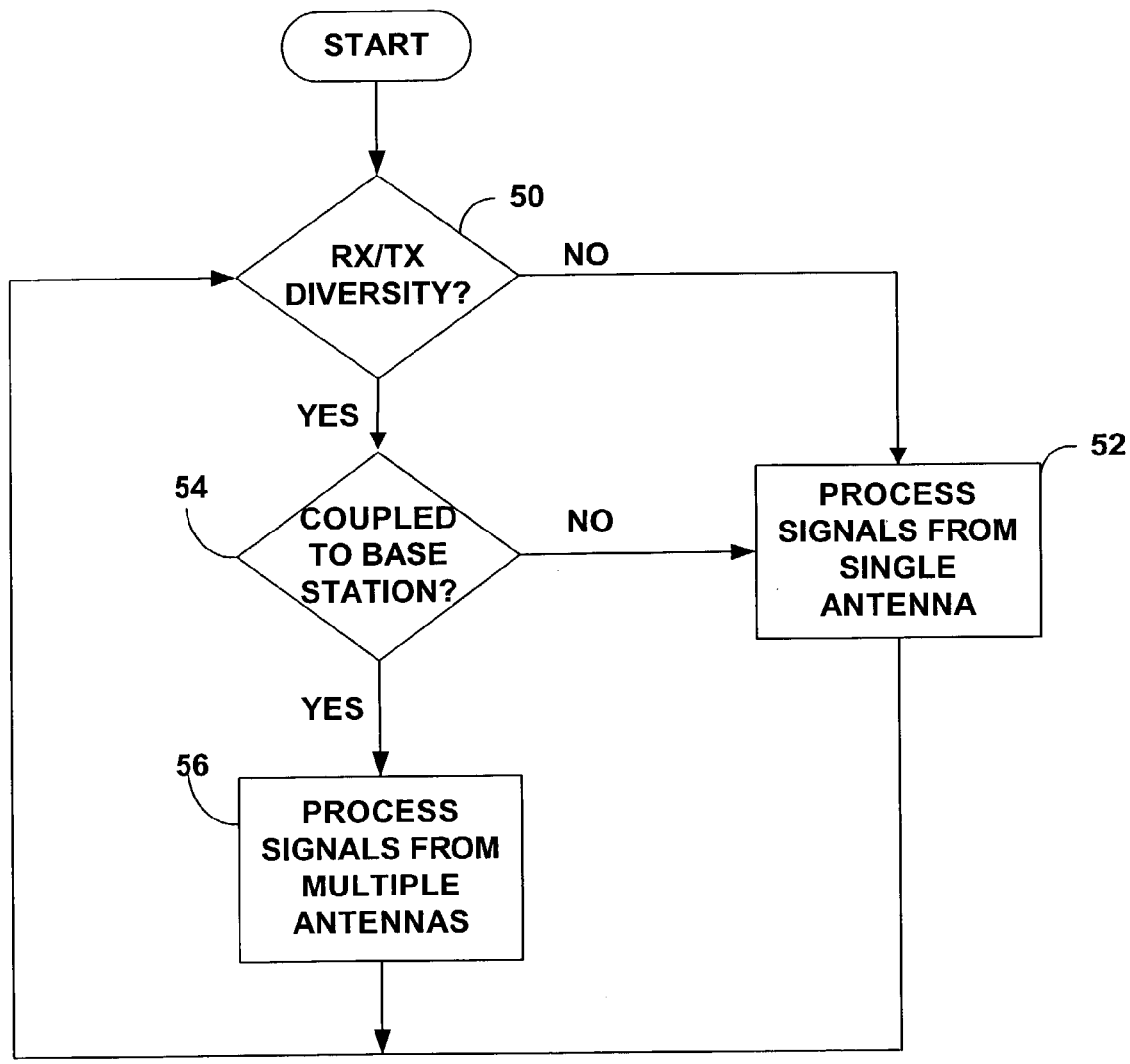
FIG. 6 is a flow diagram illustrating a process for selection of single-antenna or multi-antenna operation in a patient monitoring device.

FIG. 6 is a flow diagram illustrating a process for selection of single-antenna or multi-antenna operation in a patient monitoring device. A in FIG. 6, if monitoring device 12 is in an operating mode that supports receive/transmit (RX/TX) diversity (50). If RX/TX diversity is not supported, monitoring device 12 processes signals received and transmitted by a single antenna (58). If RX/TX diversity is supported, however, monitoring device 12 determines whether it is coupled to base station 16 (60). Monitoring device 12 may detect whether it is coupled to base station 16 by sensing signals on one or more contact terminals that engage contact terminals on the base station. If monitoring device 12 is coupled to base station 16, the monitoring device processes signals received and transmitted by multiple antennas (62). In other words, monitoring device 12 provides spatial diversity when it is coupled to base station 16. In this case, monitoring device may offer enhanced communication with IMD 14.

Figure 7:
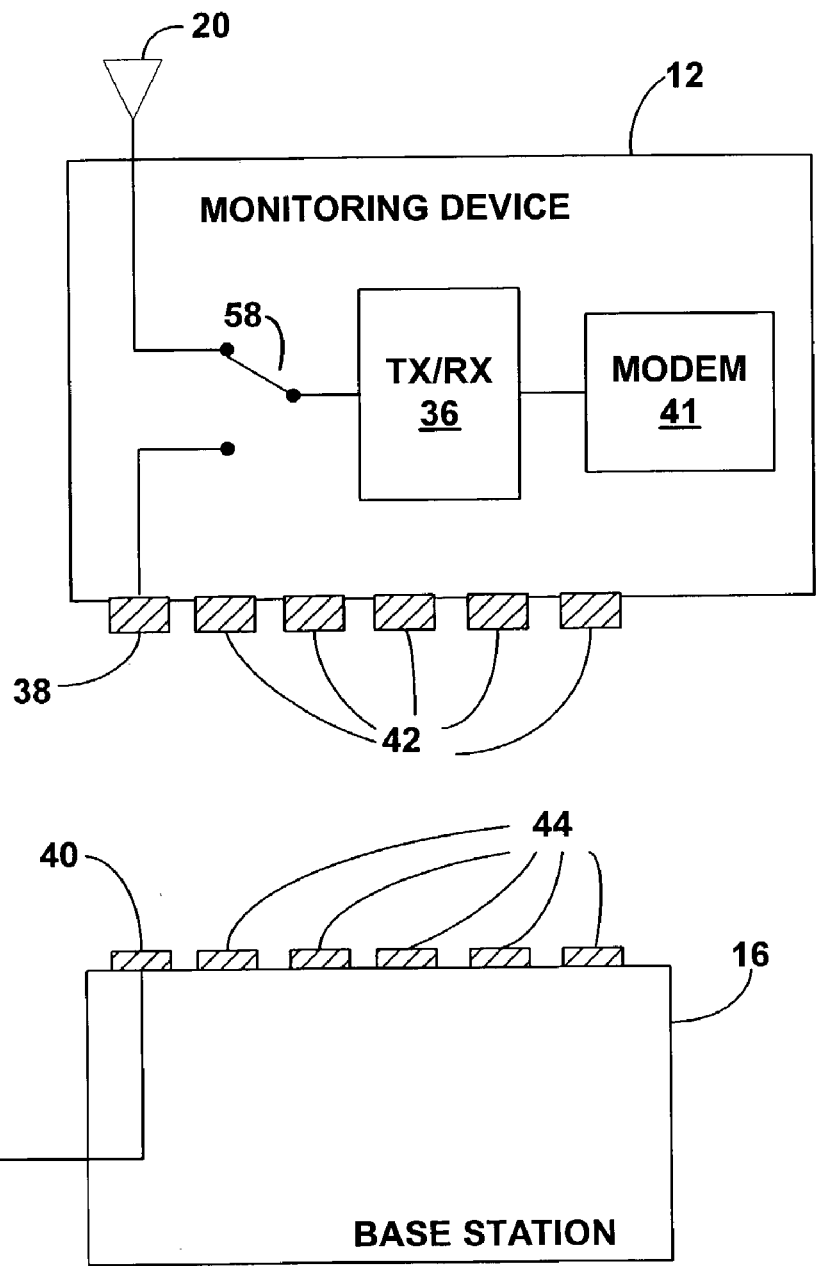
FIG. 7 is a block diagram illustrating connection of a patient monitoring device and a base station in accordance with an added embodiment of the invention.

FIG. 7 is a block diagram illustrating connection of a patient monitoring device and a base station in accordance with an added embodiment of the invention. The example of FIG. 7 conforms substantially to that of FIG. 3. Instead of providing spatial diversity operation, however, patient monitoring device 12 includes a switch 58 that permits operation using either antenna 20 associated with the patient monitoring device, or antenna 22 associated with base station 16. Antenna 22 of base station 16 may be a higher quality antenna relative to antenna 20 of patient monitoring device 12. For example, antenna 22 may have larger or more favorable dimensions, or be made of more favorable materials, than antenna 20 due to size, space, complexity or cost limitations associated with patient monitoring device 12.

Switch 58 may be configured to select one of antennas 20, 22 for used by RX/TX circuitry 36. If patient monitoring device 12 is not coupled to base station 16, switch 58 selects antenna 20. On the other hand, if patient monitoring device 12 is coupled to base station 16, switch 58 selects the higher quality antenna 22 for enhanced communication with IMD 14. In other words, in the exemplary embodiment of FIG. 7, patient monitoring device 12 may be configured to use antenna 22 instead of antenna 20 when antenna 22 is available for use. As a further alternative, antenna 22 may incorporate two more antennas for spatial diversity operation. In this case, switch 58 may couple multiple antennas from base station 16 to RX/TX circuitry 36, enabling spatial diversity communication by patient monitoring device 12 when it is coupled to base station 16.

Various embodiments of the invention have been described. These and other embodiments are within the scope of the following claims.

The invention claimed is:

1. A system comprising:
   an implantable medical device;
   a base station having a first antenna; and
   a monitoring device having a second antenna; and
   means for selectively coupling the base station to the monitoring device;
   wherein the monitoring device uses spatial diversity to communicate with the implantable medical device when the monitoring device is coupled to the base station and receives wireless signals from the implantable medical device via both a communication link to the first antenna and a communication link to the second antenna.

2. The system of claim 1, wherein the monitoring device receives the wireless signals from the implantable medical device via only the second antenna when the monitoring device is not coupled to the base station.

3. The system of claim 1, wherein the base station includes a cradle to receive the monitoring device.

4. The system of claim 1, wherein the monitoring device includes a spatial diversity receiver to process the signals received via the first antenna and the second antenna.

5. The system of claim 4, wherein the monitoring device includes a first terminal, and the base station includes a cradle to receive the monitoring device and a second terminal to mate with the first terminal and thereby connect the first antenna to the receiver.

6. The system of claim 1, wherein the base station includes a communication link to a network.

7. The system of claim 1, wherein the implantable medical device includes one of a cardiac stimulator, a neuro stimulator, a drug delivery device, and a physiological sensor device.

8. The system of claim 1, wherein the base station includes radio circuitry to process wireless signals received via the first antenna.

9. The system of claim 1, further comprising a network access point to connect the monitoring device to a network.

10. The system of claim 1, wherein the monitoring device further includes a transmitter to transmit wireless signals to program the implantable medical device.

11. A monitoring device for monitoring an implanted medical device, the monitoring device comprising:
    a first antenna;
    a wireless receiver coupled to the first antenna to process signals received from the implanted medical device via the first antenna; and
    a terminal to couple the receiver to a second antenna associated with a base station to process signals received from the implanted medical device via the second antenna, wherein the terminal is configured to mate with a second terminal in a cradle associated with the base station and thereby connect the receiver to the second antenna.

12. The monitoring device of claim 11, wherein the receiver includes a spatial diversity receiver to process the signals received via only the first antenna and the second antenna.

13. The monitoring device of claim 11, wherein the implantable medical device includes one of a cardiac stimulator, a neuro stimulator, a drug delivery device, and a physiological sensor device.

14. The monitoring device of claim 11, wherein the monitoring device further includes a transmitter to transmit wireless signals to program the implantable medical device.

15. A method comprising:
    receiving wireless signals from an implantable medical device via both a first antenna associated with a monitoring device and a second antenna associated with a base station when the monitoring device is coupled to the base station; and
    receiving the wireless signals via only the first antenna when the monitoring device is not coupled to the base and
    coupling the monitoring device to the second antenna by placing the monitoring device in a cradle defined by the base station.

16. The method of claim 15, wherein the monitoring device includes a spatial diversity receiver, the method further comprising processing the wireless signals received via the first antenna and the second antenna using the spatial diversity receiver.

17. The method of claim 15, wherein the implantable medical device includes one of a cardiac stimulator, a neuro stimulator, a drug delivery device, and a physiological sensor device.

18. The method of claim 15, further comprising transmitting wireless signals from the monitoring device to program the implantable medical device.

19. A system comprising:
    an implantable medical device;
    a base station having a first antenna; and
    a monitoring device having a second antenna, wherein the monitoring device receives wireless signals from the implantable medical device via the first antenna when the monitoring device is coupled to the base station, wherein the monitoring device includes a first terminal, and the base station includes a cradle to receive the monitoring device and a second terminal to mate with the first terminal and thereby connect the first antenna to the receiver.

20. The system of claim 19, wherein the monitoring device receives the wireless signals from the implantable medical device via only the second antenna when the monitoring device is not coupled to the base station.

21. The system of claim 19, wherein the implantable medical device includes one of a cardiac stimulator, a neuro stimulator, a drug delivery device, and a physiological sensor device.

22. A monitoring device for monitoring an implanted medical device, the device comprising:
- a first antenna;
- a wireless receiver that processes signals received from the implanted medical device via the first antenna wherein the monitoring device is not coupled to a base station; and
- a terminal that couples the wireless receiver to a second antenna associated with the base station to enable the wireless receiver to process signals received from the implanted medical device via the second antenna when the monitoring device is coupled to the base station, wherein the terminal is configured to mate with a second terminal in a cradle associated with the base station and thereby connect the receiver to the second antenna.

23. The monitoring device of claim 22, wherein the implantable medical device includes one of a cardiac stimulator, a neuro stimulator, a drug delivery device, and a physiological sensor device.

24. A method comprising:
- receiving wireless signals from an implantable medical device via a first antenna associated with a monitoring device when the monitoring device is not coupled to a base station;
- receiving wireless signals from the implantable medical device via a second antenna associated with the base station when the monitoring device is coupled to the base station; and
- coupling the monitoring device to the second antenna by placing the monitoring device in a cradle defined by the base station.

25. The method of claim 24, wherein the implantable medical device includes one of a cardiac stimulator, a neuro stimulator, a drug delivery device, and a physiological sensor device.

* * * * *